United States Patent [19]

Cohen

[11] 4,011,010
[45] Mar. 8, 1977

[54] VISUAL FIELD TESTER WHICH IS ENTITLED MULTISCALE PERIMETER

[76] Inventor: Allen L. Cohen, 9677 Basket Ring Road, Columbia, Md. 21045

[22] Filed: Feb. 18, 1976

[21] Appl. No.: 659,092

[52] U.S. Cl. ............................................. 351/24
[51] Int. Cl.² ......................................... A61B 3/02
[58] Field of Search ............................ 351/23, 24

[56] References Cited
UNITED STATES PATENTS 3,421,498  1/1969  Garrs ............................. 351/24 X
3,482,905  12/1969  Tovini ........................... 351/24 X Primary Examiner—Paul A. Sacher

[57] ABSTRACT

A multiscale perimeter is a device which has a curved surface for examining the peripheral field of vision, and which has an opening in its central portion to allow view of a surface set at a greater distance from the patient's eye to permit a more magnified examination of the central field of vision.

2 Claims, 4 Drawing Figures

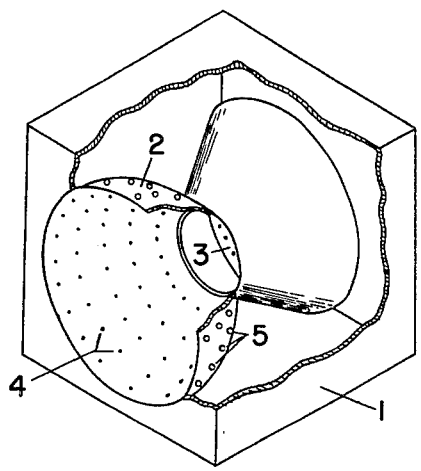
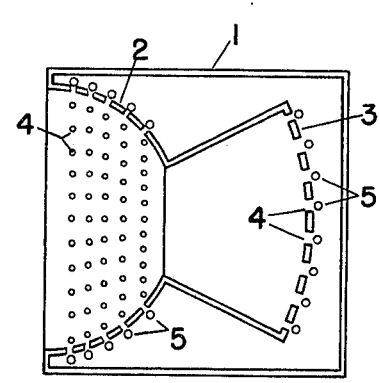
Fig. 1
Fig. 2
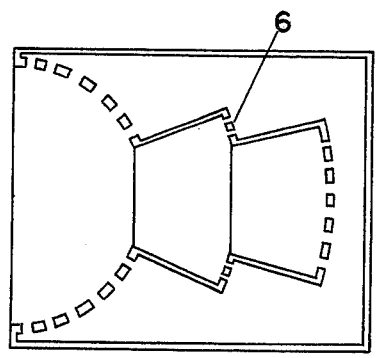
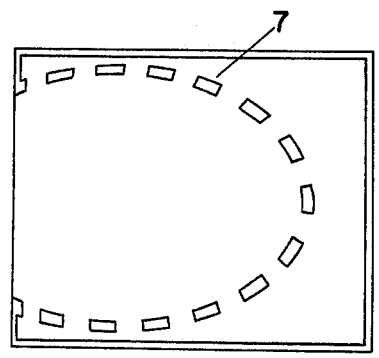
Fig. 3
Fig. 4

VISUAL FIELD TESTER WHICH IS ENTITLED MULTISCALE PERIMETER

BACKGROUND OF THE INVENTION

The present invention relates to ophthalmic instruments, and in particular is concerned with those ophthalmic instruments whose primary purpose is the testing of various aspects of the field of vision of the human eye.

Visual field testing has usually required dual instrumentation regardless of the technique of perimetry. This is because central field testing requires a larger and more magnified examination of field defects than does peripheral field testing. Magnification is routinely and easily achieved by increasing the test distance, and so we usually wind up with a central field measuring device which is operated at a large distance (often 1000 mm), and a separate peripheral field measuring device which is operated at a short distance (often 330 mm).

Within the past 15 years, a number of attempts have been made to produce a single instrument for measuring both the central and the peripheral field of vision. One approach that has been taken, was to develop devices which tested the peripheral field at the same large distances used for the central field. However, this resulted in large, bulky and inconvenient instrumentation. These devices were so bulky in fact, that some of the peripheral field often had to be sacrificed, thereby defeating the purpose of the device itself.

A second approach to the problem of dual instrumentation has been based upon an erroneous argument. Peripheral field testing must be performed about the patient's eye, and therefore usually employs a device with some sort of curved surface for testing. However, central field testing need only be performed in front of the patient's eye, and for convenience has usually employed a device with a flat surface for testing. Because peripheral and central field testing, have become so associated with curved and flat testing surfaces respectively, we have seen devices which claim to test both peripheral and central fields by merely utilizing both curved and flat surfaces. Unfortunately, these surfaces have always been set at the same distance from the patient's eye and have either been too bulky for convenience when the testing distance was large, or inadequate for central field testing when the testing distance was small.

SUMMARY OF THE INVENTION

The present invention investigates a third approach to the problem. It utilizes one or more testing surfaces involving differing distances from the patient's eye within a single instrument. It is possible to do this in a convenient manner because of the fortunate circumstance, that it is the central fields which require the large magnifications and not the peripheral fields.

The invention consists of at least one portion of surface for examining the peripheral field. This portion of surface may be arc like, or hemispherical, or of any curved nature so as to be able to wrap around the patient'field of view. Further, this portion of surface must not extend centrally, or it must be transparent if it does, or in some other manner be rendered so as not to interfere with central field examining which will be performed at a larger distance.

The invention also consists of a portion of surface for examining the central field. This surface may be flat or curved, but must be set at a greater distance from the patient's eye than the peripheral surface. The extent of this surface need only subtend a visual angle comparable with the angle subtended at the patient'eye by the central portion of the peripheral surface.

Further, this invention may also consist of one or more portions of surfaces set at intermediate distances for examining the intermediate fields.

The portions of surfaces described in the preceeding three paragraphs may either be distinct and separate from each other by structural members, or they may be continuously joined to form a single surface whose parts are at differing distances from the patient's eye.

BRIEF DESCRIPTION OF THE DRAWINGS

FIG. 1 is a general diagrammatic view, with portions cut away for clarity, of one form of instrument for testing the field of vision of the human eye, according to the present invention;

FIG. 2 is a cross-sectional view of the same instrument shown in FIG. 1; and

FIGS. 3 and 4 are cross-sectional views of alternative forms of instruments according to the present invention.

DESCRIPTION OF THE PREFERRED EMBODIMENTS

In carrying the invention into effect according to one convenient mode by way of example, as shown in FIG. 1, a single instrument for testing both the peripheral and central fields of vision of the human eye includes a housing 1 containing two testing surfaces 2 and 3. The peripheral field testing surface 2 is shown hemispherical with its central portion cut out so that the patient being examined may also directly view the central field testing surface 3. The testing surfaces are substantially spaced from each other by flared-shaped spacing means 8.

The surfaces as shown in the particular configuration of FIG. 1 are perforated by a series of apertures 4 which are illuminated from behind by small light sources 5. The light sources 5 should have means for turning them on and off in predetermined groups of one or more, by a switching circuit.

In an alternative arrangement we may include a testing surface 6 set at an intermediate distance or we may choose a single testing surface 7 of varying distances from view.

I claim:

1. Apparatus for testing both the peripheral and central fields of vision of the human eye, which includes a hemispherically shaped testing surface for peripheral field testing, and at least one more testing surface substantially spaced from said hemispherical surface, said testing surfaces being spaced from each other by flared-shaped spacing means, said surfaces being joined in such a manner such that for n testing surfaces, where n is an integer, there exists n -1 surfaces whose central area is open so as to expose all of said surfaces to view, with the more central surface portions always at a greater distance from view, and with means for presenting visual targets upon the testing surfaces in a predetermined manner and location according to the discretion of the examiner.

2. A device according to claim 1, wherein the means for presenting visual targets upon the aforementioned testing surfaces, consists of said surfaces perforated with a plurality of apertures, and having means to independently illuminate each of said apertures.

* * * * *